United States Patent [19]

Hashimoto et al.

[11] Patent Number: 5,520,910
[45] Date of Patent: May 28, 1996

[54] ANTIMICROBIAL POLYMER, CONTACT LENS AND CONTACT LENS-CARE ARTICLES

[75] Inventors: Kazukichi Hashimoto; Yoshiko Inaba; Seiji Shimura, all of Tokyo; Takao Mogami, Suwa; Tadao Kojima, Suwa; Yoichi Ushiyama, Suwa, all of Japan

[73] Assignees: Nippon Chemical Industrial; Seiko Epson Corporation, both of Tokyo, Japan

[21] Appl. No.: 397,055

[22] PCT Filed: Jul. 13, 1994

[86] PCT No.: PCT/JP94/01149

§ 371 Date: Mar. 13, 1995

§ 102(e) Date: Mar. 13, 1995

[87] PCT Pub. No.: WO95/02617

PCT Pub. Date: Dec. 26, 1995

[30] Foreign Application Priority Data

Jul. 14, 1993 [JP] Japan ................... 5-174238
Jul. 15, 1993 [JP] Japan ................... 5-175288
Jul. 15, 1993 [JP] Japan ................... 5-175289

[51] Int. Cl.$^6$ .................... A61K 31/74; C08F 30/02
[52] U.S. Cl. ................. 424/78.31; 526/278; 525/329.5; 525/329.7; 525/340

[58] Field of Search .............. 526/278; 525/329.5, 525/329.7, 340; 424/78.31

[56] References Cited

U.S. PATENT DOCUMENTS 3,919,126 11/1975 Rakshys, Jr. et al. ............ 525/340
4,043,948 8/1977 Rakshys, Jr. et al. ............ 525/340

OTHER PUBLICATIONS

CA 115: 159895 pp. 25 and 5, Khashimova et al—1990.

Primary Examiner—Joseph L. Schofer
Assistant Examiner—N. Sarofim
Attorney, Agent, or Firm—Oblon, Spivak, McClelland, Maier & Neustadt

[57] ABSTRACT

An antimicrobial polymer obtained by homo- or copolymerizing a phosphonium salt type vinyl monomer, such as 2-(methacrylic acid) ethyltri-n-octylphosphonium chloride, and a contact lens and an article for its care mainly comprising an antimicrobial resin obtained by copolymerizing a polymerizable monomer and a phosphonium salt type vinyl monomer are disclosed. The antimicrobial polymer has a broad antimicrobial spectrum and produces a sufficient antimicrobial effect after a short contact time. The contact lens and article for its care are hardly effected by contamination with microorganisms while retaining excellent optical performance and processability.

8 Claims, No Drawings

5,520,910

ANTIMICROBIAL POLYMER, CONTACT LENS AND CONTACT LENS-CARE ARTICLES

TECHNICAL FIELD

This invention relates to an antimicrobial polymer having excellent antimicrobial activity which is obtained by homo- or copolymerizing a phosphonium type vinyl monomer. The invention also relates to an antimicrobial contact lens and an antimicrobial contact lens-care article which are resist contamination from bacteria, fungi, etc. and are safe and easy to handle.

BACKGROUND ART

The demands for sterilization has been increasing in daily life as well as in industrial, agricultural and food fields, and a variety of organic or inorganic antimicrobial agents are now in use.

Most of the conventional antimicrobial agents are synthetic ones with not a little toxicity. Recently, there has been progress in research in pursuit of reducing in toxicity, and development of polymer type fixed antimicrobial agents. The polymer type fixed antimicrobial agents are capable of imparting bactericidal activity to the surface of various objects and find broad application, for example, on the surface of fibers to provide antimicrobial and deodorizing fibers. Polymer type fixed antimicrobial agents heretofore reported include those comprising polymer chains, such as a vinyl polymer, polyacrylates, polymethacrylates, polyesters or polyamides, to which an antimicrobial agent is fixed as a pendant group. For example, an alkylpyridinium salt or an alkyldimethylbenzylammonium salt can be fixed to a vinyl polymer chain; a biguanide compound to a polyacrylate or polymethacrylate chain; and an alkylpyridinium salt to a polyester or polyamide chain.

Most of the reported fixed antimicrobial agents that have been put to practical use or under study are of the quaternary ammonium salt type. Although quaternary ammonium salt type fixed antimicrobial agents exhibit broad antimicrobial spectra, their antimicrobial effects produced through short time contact are insufficient.

Phosphonium salt type fixed antimicrobial agents so far proposed include polyvinylbenzylphosphonium salts as disclosed in WO92/14865.

Certain phosphonium salt compounds are known as a biologically active substance for their broad active spectra on bacteria, fungi, and algae similarly to various nitrogen-containing compounds (see Japanese Patent Laid-Open Nos. 57-204286, 63-60903, 1-93596, 2-240090, and 62-114903). However, the antimicrobial activities of these phosphonium salt type antimicrobial agents are insufficient similar to the quaternary ammonium salt type.

Japanese Patent Laid-Open No. 4-266912 discloses an antimicrobial polymer which exhibits sufficient antimicrobial effect through short time contact as well as a broad antimicrobial spectrum. However, since the monomer essential to the polymer has a low rate of polymerization, which is allowable when the monomer is homopolymerized, it is difficult to copolymerize with other monomers having greatly different polymerization rates. Further, that monomer has insufficient hydrophilic properties and, in particular, with its alkyl chain greatly extended, has poor compatibility to hydrophilic comonomers. Furthermore, the copolymers have low activities.

On the other hand, contact lenses in general use, either hard or soft, are apt to be contaminated with bacteria and fungi as microorganisms easily grow between the contact lens and the cornea with adequate moisture, temperature and nutrients.

Hard contact lenses tend to mechanically damage the cornea, causing infection with microorganisms. Those for continuous wear, which have recently been increasing are particularly dangerous. Further, bacteria, fungi, etc. may grow on the surface of hard contact lenses in a lens container, sometimes causing corneal infectious diseases.

Water-containing soft contact lenses, while comfortable to apply, are susceptible to bacteria and fungi both on the surfaces and in the inside thereof because of their own hydrophilic properties as well as their high water content, tending to cause serious infectious diseases. Moreover, they demand care in handling and involve tedious treatment for sterilization.

Under these circumstances, studies and development of contact lenses endowed with antimicrobial properties have been promoted. For example, a contact lens comprising a chitosan derivative as a matrix and a contact lens having a resin coat containing a chitosan derivative have been proposed (see Japanese Patent Laid-Open Nos. 63-217319 and 3-102313, respectively). However, the antimicrobial contact lenses proposed are unsatisfactory in optical performance and duration of antimicrobial action.

Bacteria and fungi also propagate in contact lens-care articles, such as containers, to cause secondary infection. Therefore, it has been proposed to add an antimicrobial agent to the lens soaking solution, lens cleaner, and the like, thereby to suppress propagation of microorganisms.

However, use of a large quantity of an antimicrobial agent or a potent antimicrobial agent is unfavorable to the lens and the body, especially the cornea. Hence, means for controlling microorganisms without addition of an antimicrobial agent have been studied. Resins coated with an antimicrobial substance have been proposed, but they are unsuitable for use as contact lens-care articles because of considerable elution of the antimicrobial substance during use.

Where antimicrobial properties are imparted to a contact lens per se, special care for safety is required; for a contact lens comes into direct contact with the cornea and the conjunctiva, and any substance eluted from the lens is carried by tears to the digestive tract. Accordingly, an antimicrobial substance to be incorporated into contact lenses and related articles is essentially required to have high activity and heat stability and to be firmly fixed so as not to be dissolved out. From these considerations, phosphonium salt type polymers are deemed to be suitable.

Where an antimicrobial phosphonium type polymer is applied to contact lenses, it should be noted that the lens must exert the antimicrobial activity while retaining other properties essential to contact lenses, such as optical performance (i.e., transparency, uniformity, and heat stability), processability, strength, safety, and the like.

An object of the present invention is to solve the above-mentioned problems, and provide a novel phosphonium salt-containing polymer.

Another object of the present invention is to provide an antimicrobial agent comprising the phosphonium salt type polymer as an active ingredient, which has a broad antimicrobial spectrum and produces sufficient antimicrobial effect in a short period of contact.

A further object of the present invention is to provide a contact lens and contact lens-care articles which are substantially free from contamination by bacteria, fungi, etc. and from which the antimicrobial substance barely dissolves out.

DISCLOSURE OF INVENTION

As a result of extensive investigations, the present inventors have accomplished the above objects of the present invention.

The present invention provides an antimicrobial polymer obtained by homo- or copolymerizing at least one phosphonium salt type vinyl monomer selected from the group consisting of a compound represented by formula (1):

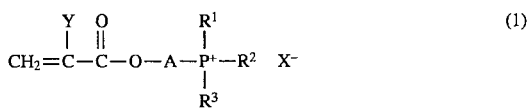

a compound represented by formula (2):

and a compound represented by formula (3):

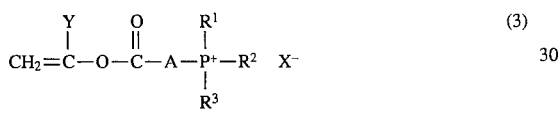

wherein A represents a linear or branched alkylene group; Y represents a hydrogen atom, a lower alkyl group or an aryl group; $R^1$, $R^2$, and $R^3$, which may be the same or different, each representing a hydrogen atom, a linear or branched alkyl group having from 1 to 18 carbon atoms, an aryl group, an aralkyl group, or an alkyl, aryl or aralkyl group which is substituted with a hydroxyl group or an alkoxy group; and $X^-$ represents an anion, either among themselves or with other copolymerizable monomers.

The present invention also provides an antimicrobial polymer obtained by homo- or copolymerizing at least one vinyl monomer selected from the group consisting of a compound represented by formula (4):

a compound represented by formula (5):

and a compound represented by formula (6):

wherein A and Y are as defined above; and X represents a monovalent atom or residual group capable of becoming an anion, either among themselves or with other copolymerizable monomers and converting the functional group of the resulting polymer to a phosphonium ion with a triorganophosphine represented by formula (7):

wherein $R^1$, $R^2$, and $R^3$ are as defined above.

The present invention further provides an antimicrobial agent containing the above-mentioned antimicrobial polymer as an active ingredient.

The present invention still further provides a contact lens mainly comprising an antimicrobial resin obtained by copolymerizing a polymerizable monomer and a phosphonium salt type vinyl monomer.

The present invention yet further provides a contact lens endowed with antimicrobial activity which is obtained by graft polymerizing a phosphonium salt type vinyl monomer to a contact lens resin.

The present invention furthermore provides a contact lens-care article mainly comprising an antimicrobial resin obtained by copolymerizing a polymerizable monomer and a phosphonium salt type vinyl monomer.

The present invention also provides the contact lens care article wherein the contact lens-care article as referred to above includes containers for contact lenses, containers for soaking solution for contact lenses, containers for contact lens cleaner, containers for cleaning soaking solution for contact lenses, containers for water for dissolving, mats for preventing contact lenses from being misplaced during washing, contact lens cases, and contact lens compact cases.

The present invention further provides a contact lens which includes those in which the phosphonium salt type vinyl monomer is selected from the group consisting of a compound represented by formula (8):

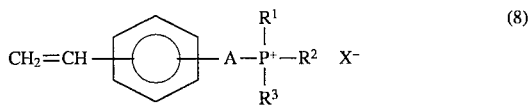

wherein A, $R^1$, $R^2$, $R^3$, and $X^-$ are as defined above, and the compounds represented by formulae (1), (2), and (3).

The present invention further provides a contact lens care article which includes those in which the phosphonium solt type vinyl monomer is at least one monomer selected from the group consisting of monomers represented by formulae (1), (2), (3) and (8).

The present invention will be illustrated in detail as below.

In the phosphonium salt type vinyl monomers represented by formulae (1), (2), and (3), A is exemplified by a linear or branched alkylene group, such as a methylene group, an ethylene group, a trimethylene group, a tetramethylene group, a pentamethylene group, a propylene group, and an ethylethylene group.

Y represents a hydrogen atom; a lower alkyl group, such as a methyl group, an ethyl group or a propyl group; or an aryl group, such as a phenyl group; with a hydrogen atom or a lower alkyl group being preferred.

$X^-$ is an anion, such as a halide ion (e.g., a fluoride ion, a chloride ion, a bromide ion or an iodide ion); aliphatic or aromatic carboxylate ion, such as a formate ion, an acetate ion, an oxalate ion, a benzoate ion or a phthalate ion; a sulfate ion; a phosphate ion, such as a methyl or dimethyl phosphate ion or an ethyl or diethyl phosphate ion; an antimony fluoride ion; a phosphorus fluoride ion; an arsenic fluoride ion; a boron fluoride ion; a perchlorate ion; an alkylsulfonate ion, such as a methanesulfonate ion; a substituted or unsubstituted benzenesulfonate ion, such as a p-toluenesulfonate ion; with a halide ion being preferred.

$R^1$, $R^2$ and $R^3$, which may be the same or different, each represent an alkyl group, such as a methyl group, an ethyl group, a propyl group, a butyl group, a pentyl group, a hexyl group, a heptyl group, an octyl group, a dodecyl group or an octadecyl group; an aryl group, such as a phenyl group, a tolyl group or a xylyl group; an aralkyl group, such as a benzyl group or a phenethyl group; or the foregoing alkyl, aryl or aralkyl group substituted with a hydroxyl group or an alkoxy group. $R^1$, $R^2$, and $R^3$ each preferably represent an alkyl group, such as a butyl group or an octyl group, or an aryl group, such as a phenyl group or a tolyl group, and still preferably an octyl group or a phenyl group.

Specific examples of the phosphonium salt type vinyl monomer represented by formula (1) are (methyl methacrylate)tri-n-butylphosphonium chloride, (methyl methacrylate)tri-n-octylphosphonium chloride, (methyl methacrylate)dimethyl-n-octadecylphosphonium chloride, (methyl methacrylate)tri-n-butylphosphonium bromide, (methyl methacrylate)tri-n-octylphosphonium bromide, 2-(methacrylic acid)ethyltri-n-butylphosphonium chloride, 2-(methacrylic acid)ethyltri-n-octylphosphonium chloride, 3-(methacrylic acid)propyltri-n-octylphosphonium chloride, 4-(methacrylic acid)butyltri-n-octylphosphonium chloride, 2-(methacrylic acid)ethyltri-n-octylphosphonium bromide, 3-(methacrylic acid)propyltri-n-octylphosphonium bromide, 4-(methacrylic acid)butyltri-n-octylphosphonium bromide, (methyl acrylate)tri-n-butylphosphonium chloride, (methyl acrylate)tri-n-octylphosphonium chloride, (methyl acrylate)dimethyl-n-octadecylphosphonium chloride, (methyl acrylate)tri-n-octylphosphonium bromide, (methyl acrylate)dimethyl-n-octadecylphosphonium bromide, (methyl acrylate)tri-n-butylphosphonium tetrafluoroborate, 2-(acrylic acid)ethyltri-n-octylphosphonium bromide, and 3-(acrylic acid)propyltri-n-octylphosphonium bromide.

Specific examples of the phosphonium salt type vinyl monomer represented by formula (2) are tri-n-butylallylphosphonium chloride, tri-n-propylallylphosphonium chloride, tri-n-octylallylphosphonium chloride tri-n-decylallylphosphonium chloride, dimethyl-n-octadecylallylphosphonium chloride, tri-n-octylallylphosphonium bromide, dimethyl-n-octadecylallylphosphonium bromide, and tri-n-octylallylphosphonium tetrafluoroborate.

Specific examples of the phosphonium salt type vinyl monomer represented by formula (3) include vinoxycarbonylmethyltri-n-butylphosphonium chloride, vinoxycarbonylmethyltri-n-propylphosphonium chloride, vinoxycarbonylmethyltri-n-octylphosphonium chloride, vinoxycarbonylmethyltri-n-decylphosphonium chloride, vinoxycarbonylmethyldimethyl-n-octadecylphosphonium chloride, vinoxycarbonylmethyltri-n-octylphosphonium bromide, vinoxycarbonylmethyldimethyl-n-octadecylphosphonium bromide, and vinoxycarbonylmethyltri-n-butylphosphonium tetrafluoroborate.

The polymer obtained by homopolymerizing the phosphonium salt type vinyl monomer represented by formula (1) includes those comprising a repeating unit represented by formula (9):

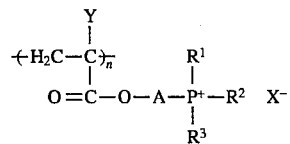
(9)

wherein $R^1$, $R^2$, $R^3$, Y, A, and $X^-$ are as defined above; and n is an integer of 2 or greater.

The polymer obtained by homopolymerizing the phosphonium salt type vinyl monomer represented by formula (2) includes those comprising a repeating unit represented by formula (10):

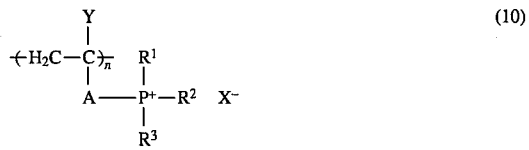
(10)

wherein $R^1$, $R^2$, $R^3$, Y, A, and $X^-$ are as defined above; and n is an integer of 2 or greater.

The polymer obtained by homopolymerizing the phosphonium salt type vinyl monomer represented by formula (3) includes those comprising a repeating unit represented by formula (11):

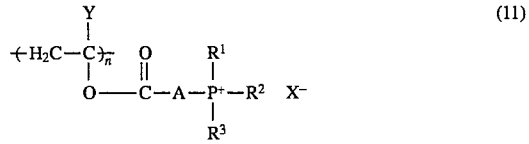
(11)

wherein $R^1$, $R^2$, $R^3$, Y, A, and $X^-$ are as defined above; and n is an integer of 2 or greater.

Of these phosphonium salt-containing homopolymers of formulae (9), (10), and (11), those in which $R^1$, $R^2$, and $R^3$ is each a lower alkyl group, such as methyl, ethyl, propyl or butyl, are soluble in water and organic solvents, such as alcohols. As the alkyl groups represented by $R^1$, $R^2$ and $R^3$ become higher such as pentyl, hexyl or octyl, the water-solubility is reduced. Those in which one of $R^1$, $R^2$, and $R^3$ is a higher alkyl group like an octadecyl group ($C_{18}$), with the other two each being a lower alkyl group like a methyl group, are also highly hydrophilic and show an enhanced attack on cell membranes, thereby exhibiting high antimicrobial activity. Those in which $X^-$ is an antimony fluoride ion, a phosphorus fluoride ion, an arsenic fluoride ion, a boron fluoride ion, or a perchlorate ion are water-insoluble irrespective of $R^1$, $R^2$, and $R^3$. In other words, the phosphonium-containing polymers of the present invention can be designed arbitrarily so as to have desired behavior to water from water-soluble or water-dispersible to water-insoluble depending on the use by altering the substituents $R^1$, $R^2$ and $R^3$ and the anion $X^-$. The antimicrobial effect of the phosphonium-containing polymers depends on the length of the alkyl groups represented by $R^1$, $R^2$ and $R^3$. For example, the antimicrobial effect increases in the order of methyl, ethyl, butyl, and octyl groups. Where one of $R^1$, $R^2$ and $R^3$ is a higher alkyl group such as an octadecyl group with the other two being a lower alkyl group such as a methyl group, the antimicrobial effect will be increased further.

The polymerizable monomers which can be copolymerized with the aforesaid phosphonium salt type vinyl monomers are generally employed radical polymerizable compounds, such as those containing at least one of a vinyl group, an allyl group, an acrylic group, a methacrylic group, etc. Examples of such copolymerizable monomers include (meth)acrylic esters, such as (meth)acrylates, alkyl (meth)acrylates, halogenated alkyl (meth)acrylates, siloxanylalkyl (meth)acrylates, fluoro(meth)acrylates, hydroxyalkyl (meth)acrylates, polyethylene glycol (meth)acrylate, (meth)acrylic esters of polyhydric alcohols, and vinyl (meth)acrylate; acrylamide and derivatives thereof; styrene and derivatives thereof; vinyl compounds, such as N-vinyllactams and vinyl (poly)carboxylate; butylene; and allyl compounds, such as allyl (poly)carboxylates and allyl carbonate. Specific examples of these monomers are ethylene, propylene, butylene, isobutylene, diisobutylene, vinyl chloride, vinylidene chloride, vinylidene bromide, vinyl alcohol, vinylacetic acid, a vinylsulfonic acid salt, vinyltoluene, cinnamic acid, vinylthiophene, vinylpyridine, vinylimidazole, styrene, methylstyrene, dimethylstyrene, chlorostyrene, dichlorostyrene, bromostyrene, p-chloromethylstyrene, divinylbenzene, acrylic acid, methyl acrylate, ethyl acrylate, n-butyl acrylate, phenyl acrylate, phenoxyethyl acrylate, tetrahydrofurfuryl acrylate, 2-hydroxyethyl acrylate, 2-hydroxypropyl acrylate, 2-acryloyloxyethylsuccinic acid, 2-acryloyloxyethylphthalic acid, methacrylic acid, methyl methacrylate, ethyl methacrylate, n-butyl methacrylate, 2-ethylhexyl methacrylate, isobornyl methacrylate, benzyl methacrylate, phenyl methacrylate, dicyclopentanyl methacrylate, dicyclopentenyl methacrylate, 2-methacryloyloxyethylsuccinic acid, 2-hydroxyethyl methacrylate, 2-hydroxypropyl methacrylate, 2-hydroxybutyl methacrylate; fumaric acid, maleic acid, itaconic acid, and esters of these acids; acrylonitrile, methacrylonitrile, acrylamide, N,N-dimethylacrylamide, N-vinyl-2-pyrrolidone, maleic anhydride, and N-substituted maleimide.

The phosphonium salt type vinyl monomer content in the copolymer usually ranges from 0.05 to 20% by weight.

A further characteristic of the present invention is that the antimicrobial polymers of the present invention can also be obtained by first homo- or copolymerizing at least one vinyl monomer represented by formula (4), (5) or (6) either alone or among themselves or with other copolymerizable monomers and then converting the functional group of the resulting polymer to a phosphonium ion by using a triorganophosphine represented by formula (7).

The triorganophosphine of formula (7) includes tri-n-butylphosphine, tri-n-propylphosphine, tri-n-octylphosphine, tri-n-decylphosphine, and dimethyl-n-octadecylphosphine.

The degree of polymerization of the antimicrobial polymers of the present invention is not particularly limited as long as it is at least 2. It usually ranges from 2 to 5000, preferably from 10 to 5000, and still preferably from 10 to 200.

The antimicrobial polymers of the invention exhibit broad antimicrobial spectra on a wide variety of bacteria, fungi, and algae. Their effects are particularly remarkable on eumycetes. They also exert an excellent antimicrobial effect on multi-resistant *Staphylococcus aureaus* (MRSA).

The antimicrobial polymers of the invention may be used in combination with carriers or other organic and/or inorganic bactericidal agents or antimicrobial agents depending upon the end use. The carriers to be used are not limited. For example, these are liquid carriers, such as water and organic solvents, e.g., alcohols and acetone; and finely powdered inorganic carriers, such as talc, kaolin, silica, alumina, magnesia, and titanium dioxide. If desired, the antimicrobial polymer may also be used in combination with adjuvants, such as surface active agents and emulsifying agents.

The phosphonium-containing polymers of the present invention are useful as antimicrobial agents for external use, antimicrobial agents for hygienic finishing of fiber, fabric, etc., coatings, constructive materials, antimicrobial agents for swimming pool water or industrial water, antimicrobial resin household articles, antimicrobial plastic articles, particularly contact lenses and contact lens-care articles, antimicrobial chopping boards, and water-absorbing resins. The antimicrobial polymer in the form of spheres or pellets may be packed into a column, etc. for use as a filter for sterilization of air or water.

The antimicrobial resin which can be used as contact lenses and contact lens-care articles is a copolymer of a polymerizable monomer and a phosphonium salt type vinyl monomer contributory to antimicrobial properties.

The term "contact lens-care articles" as used herein means all the resin articles relative to handling of contact lenses including cleaning, storage, sterilization, rinsing, and the like. Such contact lens-care articles include containers for contact lenses, containers for soaking solution for contact lenses, containers for contact lens cleaner, containers for cleaning soaking solution for contact lenses, containers for water for dissolving, mats for preventing contact lenses from being misplaced during washing, contact lens cases, and contact lens compact cases.

The antimicrobial resin to be used as contact lenses and contact lens-care articles can be prepared by using, as antimicrobial components, the above-described polymerizable monomer and a phosphonium salt type vinyl monomer represented by formula (1), (2) or (3). In addition, a phosphonium salt type vinyl monomer represented by formula (8):

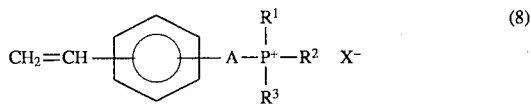

wherein $R^1$, $R^2$, $R^3$, A, and $X^-$ are as defined above, can also be used suitably as a phosphonium salt type vinyl monomer.

Specific examples of the phosphonium salt type vinyl monomer represented by formula (8) include tri-n-butyl-3(and 4)-vinylbenzylphosphonium chloride, tri-n-propyl-3(and 4)-vinylbenzylphosphonium chloride, tri-n-octyl-3(and 4)-vinylbenzylphosphonium chloride, tri-n-decyl-3(and 4)vinylbenzylphosphonium chloride, dimethyltri-n-octadecyl-3(and 4)-vinylbenzylphosphonium chloride, tri-n-octyl-3(and 4)-vinylbenzylphosphonium bromide, dimethyltri-n-octadecyl-3(and 4-vinylbenzylphosphonium bromide, and tri-n-octyl-3(and 4)-vinylbenzylphosphonium tetrafluoroborate.

In order to improve the crosslinking density of the antimicrobial resins, polyfunctional monomers, such as ethylene glycol diacrylate, diethylene glycol diacrylate, triethylene glycol diacrylate, 1,6-hexanediol diacrylate, ethylene glycol dimethacrylate, diethylene glycol dimethacrylate, triethylene glycol dimethacrylate, propylene glycol dimethacrylate, trimethylolpropane trimethacrylate, pentaerythritol triacrylate, 1,4-butanediol dimethacrylate, 1,6-hexanediol dimethacrylate, glycerin dimethacrylate, divinylbenzene diallyl phthalate, and diethylene glycol bisallylcarbonate, may also be used in combination.

The phosphonium salt type vinyl monomer content in the antimicrobial resins varies depending on the physical properties of the monomers and the end use, and is selected appropriately within such a range that the resin retains transparency while manifesting antimicrobial properties. In many cases, the recommended phosphonium salt type vinyl monomer content in the resin ranges from 0.01 to 20% by weight, particularly from 0.1 to 5% by weight. If it is less than 0.01% by weight, the antimicrobial effect would be insubstantial. If it exceeds 20% by weight, the compatibility with the polymerizable monomer is reduced so that the resulting contact lens tends to suffer from white opaqueness or haze, losing such lens functions as transparency, water content, strength, and processability.

The above-mentioned phosphonium salt type vinyl monomers or polymerizable monomers may be used either individually or in combinations of two or more thereof.

Method of Producing Antimicrobial Polymers of the Present Invention

The antimicrobial polymers according to the present invention may be prepared by any process. For example, polymerization can be carried out in the presence of a general polymerization initiator by heating or irradiating with active energy rays, such as ultraviolet light.

In some detail, a monomer(s) selected from the phosphonium salt type vinyl monomers of formulae (1), (2) and (3) or a monomer mixture comprising the phosphonium salt type vinyl monomer(s) and other copolymerizable monomer(s) is dissolved in an appropriate solvent, and a polymerization initiator is added thereto. Useful solvents include water, ethanol, dimethylformamide, benzene or a mixture thereof. Suitable polymerization initiators include radical initiators, such as benzoyl peroxide, t-butyl peroxy-2-ethylhexanoate, t-butyl peroxyisobutyrate, t-butyl peroxyisopropyl carbonate, lauroyl peroxide, azobis(2,4-dimethylvaleronitrile), 2,2'-azobis( 2-amidinopropane) hydrochloride, 2,2'-azobisisobutyronitrile, benzoyl peroxide, t-butyl hydroperoxide, di-isopropyl peroxydicarbonate, t-butyl peroxypivalate, and t-butyl peroxyneodecanoate. In the case of radiation polymerization, a photopolymerization initiator, such as benzoin ether, and, if desired, a sensitizer are used. The initiator is preferably used in amounts of from 0.001 to 5% by weight. While the reaction temperature and time are subject to variation according to the kind of the polymerization initiator used, the reaction is usually performed at 40° to 100° C. for at least 0.5 hour, preferably 1 to 24 hours. The reaction is preferably conducted in an inert atmosphere. After completion of the reaction, the reaction mixture is poured into a large quantity of acetone, tetrahydrofuran or n-hexane, and the precipitate thus formed is collected to obtain the antimicrobial polymer.

Alternatively, the antimicrobial polymer of the present invention can be prepared by polymerizing a monomer(s) selected from the vinyl monomers represented by formulae (4), (5) and (6) or a monomer mixture comprising the vinyl monomer(s) and other copolymerizable monomer(s) in the same manner as described above, and converting the functional group in the resulting polymer chain to a phosphonium ion with a triorganophosphine represented by formula (7).

In more detail, the monomer or the monomer mixture is dissolved in a solvent, and a polymerization initiator is added thereto to effect polymerization. The reaction mixture is worked up in the same manner as described above. The resulting polymer is dispersed in n-hexane, toluene, etc. and, while in a swollen state, reacted with a triorganophosphine of formula (7) in an inert atmosphere at 30° to 150° C. , preferably 70° to 120° C., for 5 to 48 hours, preferably 10 to 20 hours, to obtain the antimicrobial polymer.

The Method of Producing a Contact Lens and Contact Lens-care Article

The contact lens of the present invention is suitably produced by injecting a monomer mixture containing at least one of the phosphonium salt type monomers of formulas (1), (2), (3) and (8), a copolymerizable monomer and, if desired, a polyfunctional monomer for increasing a crosslinking density into a glass tube, a polypropylene- or polytetrafluoroethylene-tube or a space in sheet form and subjected to thermal polymerization under heating or photopolymerization under ultraviolet irradiation. In cases where the resulting polymer will be subject to strain due to shrinkage or heat, it is preferably subjected to annealing by heating. If desired, the polymerization system may contain small amounts of thermal stabilizers, antioxidants, colorants, ultraviolet absorbents, and so on.

The process for producing contact lens-care articles is not particularly restricted. For example, the antimicrobial resin may be powdered and injection molded.

In another embodiment of the contact lenses and contact lens-care articles according to the present invention, the aforesaid phosphonium salt type vinyl monomer can be graft-polymerized to the surface layer of a contact lens material to impart antimicrobial properties to the material. In this case, a contact lens is subjected to a surface treatment, such as ultraviolet irradiation, corona discharge, or low-temperature plasma discharge, and the phosphonium salt type vinyl monomer is grafted to the radical generated. More specifically, the graft polymerization can be carried out by (1) a process comprising treating a lens with plasma by a glow discharge under reduced pressure of $10^{-3}$ to 10 Torr and introducing the monomer in the form of vapor or liquid into the apparatus to be directly reacted with a radical, (2) a process comprising subjecting a lens to a low-temperature plasma treatment and reacting the treated lens taken out of the apparatus with the monomer, or (3) a process comprising irradiating a lens with ultraviolet light in a solution in the presence of the antimicrobial monomer and a sensitizer to graft the monomer to the surface of the lens.

The antimicrobial polymer of the present invention, when used as an antimicrobial agent, exhibits powerful antimicrobial action as compared with conventional quaternary ammonium salt type ones. While not clear, the mechanism of the action may be accounted for as followes. Being cationic, a phosphonium salt, when polymerized, is capable of increasing a phosphonium salt concentration in the vicinity of a negatively charged microbial cell membrane. According to pharmacological studies, since a phosphonium salt is an antimicrobial agent that attacks a cell membrane, it does not need to be taken into the cell for manifesting its antimicrobial action. Therefore, reduction in cell membrane permeability of a phosphonium salt due to polymerization will not become a disadvantageous factor and so will not interfere with the manifestation of a positive polymer effect.

The contact lenses and contact lens-care articles according to the present invention are protected against contamination with microorganisms and have improved safety so that the tedious process of sterilization can be omitted.

BEST MODE FOR CARRYING OUT THE INVENTION

The present invention will now be illustrated in greater detail with reference to the Examples, but it should be understood that the present invention is not construed as being limited thereto. All the parts and percents are given by weight unless otherwise indicated.

EXAMPLE 1

1) Synthesis of Poly[2-(methacrylic acid)ethyltri-n-octylphosphonium Chloride]:

In 20 ml of water was dissolved 2.00 g (0.0039 mol) of 2-(methacrylic acid)ethyltri-n-octylphosphonium chloride represented by formula (I), and 25 ml of 2,2'-azobis-(2-amidinopropane) hydrochloride was added thereto, followed by deaeration and sealing. The system was allowed to stand at 60° C. for 6 hours to carry on polymerization. After the reaction, the reaction mixture was poured into a large excess of tetrahydrofuran, and the precipitate thus formed was collected by filtration to obtain 0.92 g of poly[2-(methacrylic acid) ethyltri-n-octylphosphonium chloride]. The degree of polymerization of the polymer was 91.

Other phosphonium salt polymers were prepared in the same manner as described above, except for replacing 2-(methacrylic acid)ethyltri-n-octylphosphonium chloride with each of the monomer compounds shown in Table 1 below.

2) Measurement of Antimicrobial Activity (Solution Dilution Method):

Each of the polymers prepared in (1) above was brought into contact with *Escherichia coli* IFO 3806 as a typical Gram negative bacterium or *Staphylococcus aureaus* IFO 12732 as a typical Gram positive bacterium under the concentration and contact time conditions shown in Tables 1 and 2. The antimicrobial activity was evaluated by a solution dilution method. The solution dilution method comprises inoculating a polymer solution at a prescribed concentration with a prescribed amount of bacterial cells and, after a prescribed contact time, counting the number of residual cells. The smaller the number of residual cells for each contact time, the more potent the antimicrobial activity of the polymer. The results obtained are shown in Tables 1 and 2.

EXAMPLE 2

1) Synthesis of Homopolymer of tri-n-butylallylphosphonium Chloride:

In 20 ml of water was dissolved 2.00 g (0.0706 mol) of tri-n-butylallylphosphonium chloride represented by formula (2), and 46 mg of 2,2'-azobis(2-amidinopropane) hydrochloride was added thereto, followed by deaeration and sealing. The system was allowed to stand at 60° C. for 6 hours to carry on polymerization. After the reaction, the reaction mixture was poured into a large excess of tetrahydrofuran, and the precipitate thus formed was collected by filtration to obtain 0.97 g of poly[tri-n-butylallylphosphonium chloride]. The degree of polymerization of the polymer was 82.

Other phosphonium salt polymers were prepared in the same manner as described above, except for replacing tri-n-butylallylphosphonium chloride with each of the trialkylallylphosphonium salts shown in Table 3 below.

2) Measurement of Antimicrobial Activity (Solution Dilution Method):

TABLE 1

| | Antimicrobial Activity on *E. coli* | | | | |
|---|---|---|---|---|---|
| | Concentration | Number of Residual Cells (/ml) | | | |
| Monomer of Formula (1) | (ppm) | Initial | 0.5 hr | 1.0 hr | 2.0 hrs |
| $R^1 = R^2 = R^3 = C_4H_9$; | 1 | $2.2 \times 10^6$ | $2.2 \times 10^6$ | $7.7 \times 10^5$ | $7.7 \times 10^5$ |
| $Y = CH_3$; $A = C_2H_4$; | 10 | $2.2 \times 10^6$ | $3.4 \times 10^5$ | $2.0 \times 10^4$ | $1.1 \times 10^3$ |
| $X = Cl$ | 100 | $2.2 \times 10^6$ | 0 | 0 | 0 |
| $R^1 = R^2 = R^3 = C_8H_{17}$; | 1 | $2.0 \times 10^6$ | $7.4 \times 10^5$ | $5.4 \times 10^5$ | $4.2 \times 10^4$ |
| $X = Cl$; $A = C_2H_4$; | 10 | $2.0 \times 10^6$ | 0 | 0 | 0 |
| $Y = CH_3$ | 100 | $2.0 \times 10^6$ | 0 | 0 | 0 |
| $R^1 = R^2 = CH_3$; $R^3 =$ | 1 | $3.0 \times 10^6$ | $4.7 \times 10^4$ | $3.4 \times 10^2$ | $5.7 \times 10$ |
| $C_{18}H_{37}$; $X = Cl$ | 10 | $3.0 \times 10^6$ | 0 | 0 | 0 |
| $Y = CH_3$; $A = C_2H_4$; | 100 | $3.0 \times 10^6$ | 0 | 0 | 0 |

TABLE 2

| | Antimicrobial Activity on *S. aureaus* | | | | |
|---|---|---|---|---|---|
| | Concentration | Number of Residual Cells (/ml) | | | |
| Monomer of Formula (1) | (ppm) | Initial | 0.5 hr | 1.0 hr | 2.0 hrs |
| $R^1 = R^2 = R^3 = C_4H_9$; | 1 | $2.1 \times 10^7$ | $4.5 \times 10^3$ | $6.1 \times 10$ | 0 |
| $Y = CH_3$; $A = C_2H_4$; | 10 | $2.1 \times 10^7$ | 0 | 0 | 0 |
| $X = Cl$ | 100 | $2.1 \times 10^7$ | 0 | 0 | 0 |
| $R^1 = R^2 = R3^-C_8H_{17}$; | 1 | $2.0 \times 10^7$ | 0 | 0 | 0 |
| $X = Cl$; $A = C_2H_4$; | 10 | $2.0 \times 10^7$ | 0 | 0 | 0 |
| $Y = CH_3$ | 100 | $2.0 \times 10^7$ | 0 | 0 | 0 |
| $R^1 = R^2 = CH_3$; $R^3 =$ | 1 | $3.0 \times 10^7$ | 0 | 0 | 0 |
| $C_{18}H_{37}$; $X = Cl$ | 10 | $3.0 \times 10^7$ | 0 | 0 | 0 |
| $Y = CH_3$; $A = C_2H_4$; | 100 | $3.0 \times 10^7$ | 0 | 0 | 0 |

The antimicrobial activity of each of the polymers prepared in (1) above was measured in the same manner as in Example 1-(2). The results obtained are shown in Tables 3 to 5.

TABLE 3

| | Antimicrobial Activity on *E. coli* | | | | |
|---|---|---|---|---|---|
| Monomer of | Concentration | Number of Residual Cells (/mi) | | | |
| Formula (2) | (ppm) | Initial | 0.5 hr | 1.0 hr | 2.0 hrs |
| Control | 0 | $6.0 \times 10^4$ | $6.3 \times 10^4$ | $5.7 \times 10^4$ | $4.0 \times 10^4$ |

TABLE 3-continued

Antimicrobial Activity on E. coli

| Monomer of Formula (2) | Concentration (ppm) | Number of Residual Cells (/ml) | | | |
|---|---|---|---|---|---|
| | | Initial | 0.5 hr | 1.0 hr | 2.0 hrs |
| $R^1 = R^2 = R^3 = C_4H_9$; | 1 | $6.0 \times 10^4$ | $6.0 \times 10^4$ | $4.5 \times 10^4$ | $3.4 \times 10^4$ |
| X = Cl | 10 | $6.0 \times 10^4$ | $4.8 \times 10^4$ | $2.3 \times 10^4$ | $3.4 \times 10^3$ |
| | 100 | $6.0 \times 10^4$ | $1.6 \times 10^4$ | $3.2 \times 10^3$ | $1.6 \times 10^2$ |
| $R^1 = R^2 = R^3 = C_8H_{17}$; | 1 | $6.0 \times 10^4$ | $8.8 \times 10^3$ | $7.4 \times 10^2$ | 0 |
| X = Cl | 10 | $6.0 \times 10^4$ | 30 | 0 | 0 |
| | 100 | $6.0 \times 10^4$ | 0 | 0 | 0 |

TABLE 4

Antimicrobial Activity on S. aureaus

| Monomer of Formula (2) | Concentration (ppm) | Number of Residual Cells (/ml) | | | |
|---|---|---|---|---|---|
| | | Initial | 0.5 hr | 1.0 hr | 2.0 hrs |
| Control | 0 | $4.7 \times 10^8$ | $6.3 \times 10^6$ | $4.7 \times 10^5$ | $4.0 \times 10^5$ |
| $R^1 = R^2 = R^3 = C_4H_9$; | 1 | $4.7 \times 10^6$ | $2.4 \times 10^5$ | $1.3 \times 10^4$ | $6.4 \times 10^3$ |
| X = Cl | 10 | $4.7 \times 10^6$ | $1.3 \times 10^5$ | $1.6 \times 10^3$ | 0 |
| | 100 | $4.7 \times 10^6$ | $2.0 \times 10^4$ | 0 | 0 |
| $R^1 = R^2 = R^3 = C_8H_{17}$; | 1 | $4.7 \times 10^6$ | $6.3 \times 10^2$ | 0 | 0 |
| X = Cl | 10 | $4.7 \times 10^6$ | 30 | 0 | 0 |
| | 100 | $4.7 \times 10^6$ | 0 | 0 | 0 |

TABLE 5

Antimicrobial Activity on E. coli

| Monomer of Formula (2) | Concentration (ppm) | Number of Residual Cells (/ml) | | | |
|---|---|---|---|---|---|
| | | Initial | 0.5 hr | 1.0 hr | 2.0 hrs |
| Control | 0 | $2.3 \times 10^4$ | $2.7 \times 10^4$ | $1.6 \times 10^4$ | $2.0 \times 10^4$ |
| $R^1 = R^2 = CH_3$; | 1 | $2.3 \times 10^4$ | $1.3 \times 10^3$ | $3.0 \times 10^2$ | 0 |
| $R^3 = C_{12}H_{25}$; | 10 | $2.3 \times 10^4$ | $2.0 \times 10$ | 1 | 0 |
| X = Cl | 100 | $2.3 \times 10^4$ | 0 | 0 | 0 |
| $R^1 = R^2 = CH_3$; | 1 | $2.3 \times 10^4$ | $2.4 \times 10^3$ | $4.2 \times 10^2$ | 0 |
| $R^3 = C_{14}H_{29}$; | 10 | $2.3 \times 10^4$ | $5.0 \times 10$ | 0 | 0 |
| X = Cl | 100 | $2.3 \times 10^4$ | 0 | 0 | 0 |
| $R^1 = R^2 = CH_3$; | 1 | $2.3 \times 10^4$ | $2.6 \times 10^3$ | $2.1 \times 10^2$ | 0 |
| $R^3 = C_{16}H_{33}$; | 10 | $2.3 \times 10^4$ | 83 | 4 | 0 |
| X = Cl | 100 | $2.3 \times 10^4$ | 0 | 0 | 0 |
| $R^1 = R^2 = CH_3$; | 1 | $2.3 \times 10^4$ | $7.8 \times 10^2$ | $5.5 \times 10$ | 0 |
| $R^3 = C_{18}H_{37}$ | 10 | $2.3 \times 10^4$ | 0 | 0 | 0 |
| X = Cl | 100 | $2.3 \times 10^4$ | 0 | 0 | 0 |

EXAMPLE 3

In 20 ml of water was dissolved 2.00 g (0.0038 mol) of vinoxycarbonylmethyltri-n-butylphosphonium chloride represented by formula (3), and 25 mg of 2,2'-azobis(2-amidinopropane) hydrochloride was added thereto, followed by deaeration and sealing. The system was allowed to stand at 60° C. for 6 hours to carry on polymerization. After the reaction, the reaction mixture was poured into a large excess of tetrahydrofuran, and the precipitate thus formed was collected by filtration to obtain 0.97 g of polyvinoxycarbonylmethyltri-n-butylphosphonium chloride. The degree of polymerization of the polymer was 82.

Other phosphonium salt polymers were prepared in the same manner as described above, except for replacing vinoxycarbonylmethyltri-n-butylphosphonium chloride with the vinoxycarbonylmethyltrialkylphosphonium salt shown in Tables 6 and 7 below.

The antimicrobial activity of each of the resulting polymers was measured in the same manner as in Example 1-(2). The results obtained are shown in Tables 6 and 7.

TABLE 6

Antimicrobial Activity on E. coli

| Monomer of Formula (3) | Concentration (ppm) | Number of Residual Cells (/ml) | | | |
|---|---|---|---|---|---|
| | | Initial | 0.5 hr | 1.0 hr | 2.0 hrs |
| Control | 0 | $6.6 \times 10^4$ | $6.3 \times 10^4$ | $5.7 \times 10^4$ | $4.0 \times 10^4$ |
| $R^1 = R^2 = R^3 = C_4H_9$; | 1 | $6.6 \times 10^4$ | $4.8 \times 10^4$ | $4.8 \times 10^4$ | $4.3 \times 10^3$ |
| X = Cl | 10 | $6.6 \times 10^4$ | $4.4 \times 10^4$ | $4.0 \times 10^4$ | $1.2 \times 10^3$ |
| | 100 | $6.6 \times 10^4$ | $3.9 \times 10^2$ | 20 | 0 |
| $R^1 = R^2 = R^3 = C_8H_{17}$; | 1 | $6.6 \times 10^4$ | $3.9 \times 10^3$ | $6.5 \times 10^3$ | $1.0 \times 10^2$ |
| X = Cl | 10 | $6.6 \times 10^4$ | $1.1 \times 10^2$ | 0 | 0 |

TABLE 6-continued

| | Antimicrobial Activity on *E. coli* | | | | |
|---|---|---|---|---|---|
| Monomer of | Concentration | \multicolumn{4}{c}{Number of Residual Cells (/ml)} |
| Formula (3) | (ppm) | Initial | 0.5 hr | 1.0 hr | 2.0 hrs |
| | 100 | $6.6 \times 10^4$ | 0 | 0 | 0 |

TABLE 7

| | Antimicrobial Activity on *S. aureaus* | | | | |
|---|---|---|---|---|---|
| Monomer of | Concentration | | Number of Residual Cells (/ml) | | |
| Formula (3) | (ppm) | Initial | 0.5 hr | 1.0 hr | 2.0 hrs |
| Control | 0 | $3.1 \times 10^6$ | $4.2 \times 10^6$ | $3.1 \times 10^5$ | $2.6 \times 10^5$ |
| $R^1 = R^2 = R^3 = C_4H_9$; | 1 | $3.1 \times 10^6$ | $2.7 \times 10^4$ | $5.0 \times 10^3$ | $4.2 \times 10^2$ |
| X = Cl | 10 | $3.1 \times 10^6$ | $6.3 \times 10^3$ | $1.2 \times 10^3$ | 0 |
| | 100 | $3.1 \times 10^6$ | $6.0 \times 10^3$ | 0 | 0 |
| $R^1 = R^2 = R^3 = C_8H_{17}$; | 1 | $3.1 \times 10^8$ | $2.0 \times 10^3$ | $7.9 \times 10^2$ | 7 |
| X = Cl | 10 | $3.1 \times 10^6$ | 0 | 0 | 0 |
| | 100 | $3.1 \times 10^6$ | 0 | 0 | 0 |

EXAMPLE 4

1) Copolymerization of tri-n-octylallylphosphonium chloride represented by formula (2) and methyl methacrylate:

Methyl methacrylate was thoroughly mixed with 0.2% of azobis(2,4-dimethylvaleronitrile) and 1, 10 or 50% of tri-n-octylallylphosphonium chloride, and the mixture was put in a glass test tube. After deaeration, the system was heated at 60 for 3 hours to conduct polymerization. The product was ground in a mortar and subjected to measurement of antimicrobial activity.

2) Measurement of Antimicrobial Activity (Solution Dilution Method)

The antimicobial activity on *S. aureus* IFO12372 was measured in the same manner as in Example 1 in which the copolymer was applied to 1 ml of the bacteria solution under the concentrations and contact times shown in Table 8. The results obtained are shown in Table 8 below.

was added thereto, followed by deaeration and sealing. The system was allowed to stand at 60° C. for 6 hours to conduct polymerization. To the reaction mixture was added 50.51 g (0.1300 mol) of tri-n-octylphosphine (the compound of formula (7)) was added thereto to convert the functional group of the polymer.

The antimicrobial activity of the resulting polymer on *E. coli* IFO 03806 was measured in the same manner as in Example 1. The results obtained are shown in Table 9 below.

TABLE 8

| | Antimicrobial Activity on S. aurcaus | | | | |
|---|---|---|---|---|---|
| Monomer of | Concentration | | Number of Residual Cells (/ml) | | |
| Formula (3) | (ppm) | Initial | 0.5 hr | 1.0 hr | 2.0 hrs |
| Control | 0 ppm | $8.4 \times 10^4$ | $8.8 \times 10^4$ | $8.0 \times 10^4$ | $5.6 \times 10^4$ |
| $R^1 = R^2 = R^3 = C_8H_{17}$; | 1% | $8.4 \times 10^4$ | $1.2 \times 10^4$ | $1.0 \times 10^2$ | 0 |
| X = Cl | 10 | $8.4 \times 10^4$ | $3.2 \times 10^3$ | 23 | 0 |
| | 100 | $8.4 \times 10^4$ | 42 | 0 | 0 |

EXAMPLE 5

In 40 ml of water were dissolved 5.08 g (0.0651 mol) of allyl chloride and 8.00 g (0.0650 mol) of vinyl chloroacetate, and 85 mg of 2,2'-azobis(2-amidinopropane) hydrochloride

TABLE 9

| Monomer of Formula (2) | Concentration (ppm) | Antimicrobial Activity on *E. coli* Number of Residual Cells (/ml) | | | |
|---|---|---|---|---|---|
| | | Initial | 0.5 hr | 1.0 hr | 2.0 hrs |
| Control | 0 | $6.0 \times 10^4$ | $6.3 \times 10^4$ | $5.7 \times 10^4$ | $4.0 \times 10^4$ |
| $R^1 = R^2 = R^3 = C_{18}H_{17}$; | 1 | $6.0 \times 10^4$ | $7.3 \times 10^4$ | $8.4 \times 10^2$ | 0 |
| X = Cl | 10 | $6.0 \times 10^4$ | 80 | 0 | 0 |
| | 100 | $6.0 \times 10^4$ | 0 | 0 | 0 |

EXAMPLE 6

1) Preparation of Contact Lens:

Fifty-four parts of 2,2,3,3,4,4,4-heptafluorobutyl methacrylate, 1 part of tri-n-octyl-3(or 4)-vinylbenzylphosphonium chloride represented by formula (8), 44 parts of methyldi(trimethylsiloxy)silylpropyl methacrylate, 0.7 part of ethylene glycol dimethacrylate, and 0.3 part of isopropyl percarbonate were mixed well at room temperature. The mixture was put in a glass test tube, and the test tube was deaerated and sealed with nitrogen. The test tube was heated at 28° C. for 6 hours; 30° C. for 4 hours; 32° C. for 3 hours; 40° C. for 2 hours; 50° C. for 2 hours; 60° C. for 1.5 hours; and 80° C. for 2 hours in a programmed-temperature warm water tank and then at 100° C. for 2 hours in an atmospheric furnace to conduct polymerization. The resulting resin rod was cut and polished to obtain several contact lenses.

2) Measurement of Antimicrobial Activity:

All the procedures described below were conducted aseptically.

*Escherichia coli* IFO 3806 or *Staphylococcus aureaus* ATCC 6538P was serially cultured on a slant medium at 37° C. for 16 to 24 hours to a passage number of at least 3. The culture was transferred to 8 to 10 ml of nutrient broth and further cultured at 37° C. for 16 to 24 hours to prepare a cell suspension. The cell suspension was preserved at 15° C. and used within 3 days.

The contact lenses prepared above were cold sterilized and soaked in 1 ml of the cell suspension adjusted to a cell concentration of $5.0 \times 10^5$ to $3.0 \times 10^6$ cells per ml of nutrient broth at 37° C. The cell suspension at the initial stage (contact time: 0 hr) and after a contact time of 0.5, 1 or 2 hours was diluted with a sterilized buffered physiological saline, and the antimicrobial activity of the lens was measured in accordance with a mixed dilution plate culture method (37° C.×2 days) using a medium for cell number counting (a standard agar medium produced by Eiken Kagaku K.K.).

EXAMPLE 7

Methyl methacrylate (94.8 parts), 4 parts of triethylene glycol dimethacrylate, 1 part of tri-n-octylallylphosphonium chloride represented by formula (2), and 0.2 part of azobis(2,4-dimethylvaleronitrile) were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses.

The antimicrobial activity of the lenses was evaluated in the same manner as in Example 6.

EXAMPLE 8

2-Hydroxyethyl methacrylate (95.7 parts), 2 parts of ethylene glycol dimethacrylate, 0.3 part of isopropyl percarbonate, and 1 part each of tri-n-octylvinoxycarbonylphosphonium chloride and the compounds shown in Tables 13 and 14 below (the compounds of formula (3)) were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses. The lenses were swollen and washed with pure water and immersed in physiological saline to absorb a prescribed amount of water and also to complete elution of any soluble matter. The antimicrobial activity of the lenses were evaluated in the same manner as in Example 6.

EXAMPLE 9

72.7 parts of 2,3-Dihydroxypropyl methacrylate, 25 parts of methyl methacrylate, 1 part of ethylene glycol dimethacrylate, 1 part each of tri-n-octyl(methacrylic acid)phosphonium chloride represented by formula (1) and the compounds shown in Tables 16 and 17 below (the compounds of formula (1)), and 0.3 part of isopropyl percarbonate were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses. The lenses were swollen and washed with pure water and immersed in physiological saline to absorb a prescribed amount of water and also to complete elution of any soluble matter.

The antimicrobial activity of the lenses were evaluated in the same manner as in Example 6.

EXAMPLE 10

71.95 parts of 2,3-Dihydroxypropyl methacrylate, 26 parts of methyl methacrylate, 1 part of ethylene glycol dimethacrylate, 1 part of tri-n-octylvinylbenzylphosphonium chloride, and 0.05 part of 2,4,6-trimethylbenzoyldiphenylphosphine oxide were mixed well. After deaeration and purging with nitrogen, the mixture was dropped into contact lens-shaped glass molds and irradiated with ultraviolet light using a 80 W/cm high pressure mercury lamp placed at 10 cm away for 100 seconds. The resulting contact lenses were swollen and washed with pure water and immersed in physiological saline to absorb a prescribed amount of water and also to complete elution of any soluble matter.

The antimicrobial activity of the lenses were evaluated in the same manner as in Example 6.

EXAMPLE 11

Fifty parts of N,N-dimethylacrylamide, 30.7 parts of tris(trimethylsiloxy) silylpropyl methacrylate, 17 parts of 2,2,2-trifluoroethyl methacrylate, 1 part of ethylene glycol dimethacrylate, 0.3 part of isopropyl percarbonate, and 1 part each of dimethyl-n-hexadecylallylphosphonium chloride and the compounds shown in Tables 20 and 21 below (the compounds of formula (2)) were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses. The lenses were swollen and washed with pure water and immersed in physiological saline to absorb a prescribed amount of water and also to complete elution of any soluble matter. The antimicrobial activity of the lenses were evaluated in the same manner as in Example 6.

EXAMPLE 12

1) Preparation of Contact Lens:

73.7 parts of 2,3-Dihydroxypropyl methacrylate, 25 parts of methyl methacrylate, 1 part of ethylene glycol dimethacrylate, and 0.3 part of isopropyl percarbonate were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses.

2) Plasma Treatment:

The contact lenses were subjected to a low-temperature plasma treatment in a plasma polymerization apparatus in an air atmosphere at a degree of vacuum of 0.1 Torr under conditions of a discharge frequency of 13.56 MHz and a discharge power of 200 W for 30 seconds.

3) Graft Polymerization:

The plasma-treated contact lenses were immersed in a benzene solution of tri-n-octylbenzylphosphonium chloride and heated at 60 for 1 hour to graft tri-n-octylallylphosphonium chloride (2) to the surface of the lenses.

In the same manner as described above, each of the compounds shown in Tables 23 to 25 (the compound of formula (1), (3) or (8), respectively) was graft-polymerized to a lens surface.

4) Swelling and Elution:

The resulting lenses were swollen with pure water, washed, and soaked in physiological saline to absorb a prescribed amount of water and also to complete elution of any soluble matter.

5) Measurement of Antimicrobial Activity:

The antimicrobial activity of the lenses were evaluated in the same manner as in Example 6.

EXAMPLE 13

1) Preparation of Contact Lens:

Fifty parts of N,N-dimethylacrylamide, 31.7 parts of tris(trimethylsiloxy)silylpropyl methacrylate, 17 parts of 2,2,2-trifluoroethyl methacrylate, 1 part of ethylene glycol dimethacrylate, and 0.3 part of isopropyl percarbonate were mixed well, and the mixture was put in a glass test tube. The test tube was repeatedly purged with nitrogen for deaeration and heat-sealed in vacuo. The sealed test tube was heated at 30° C. for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses.

2) UV-Induced Graft Polymerization:

The resulting contact lenses were immersed in a benzene solution containing 0.2 mol/l of benzophenone and 0.5 mol/l of tri-n-octyl-4-vinylbenzylphosphonium chloride (2) and irradiated with ultraviolet light using a mercury lamp for 5 minutes to graft an antimicrobial agent to the surface of the lenses.

In the same manner as described above, each of the compounds shown in Tables 27 to 29 (the compound of formula (1), (3) or (8), respectively) was graft-polymerized to a lens surface.

3) Swelling and Elution:

The resulting lenses were swollen with pure water, washed, and soaked in physiological saline to absorb a prescribed amount of water and also to complete elution of any soluble matter.

4) Measurement of Antimicrobial Activity:

The antimicrobial activity of the lenses were evaluated in the same manner as in Example 6.

EXAMPLE 14

1) Preparation of Antimicrobial Resin Powder:

89.8 parts of methyl methacrylate, 10 parts each of tri-n-octylallylphosphonium chloride (2) and the compounds shown in Tables 31 to 33 (the compound of formula (1), (3) or (8), respectively), and 0.2 part of azobis(2,4-dimethylvaleronitrile) were mixed well, and the mixture was put in a glass test tube. The test tube was purged with nitrogen for deaeration and heat-sealed. The sealed test tube was heated in warm water at 70° C. for 6 hours to conduct polymerization. The resulting resin rod was ground to powder to prepare a powdered antimicrobial resin.

2) Preparation of Contact Lens Container:

Ten parts of the powdered antimicrobial resin prepared in (1) above were thoroughly mixed with 90 parts of polyethylene, and the mixture was injection molded to obtain several contact lens containers.

3) Measurement of Antimicrobial Activity:

The antimicrobial activity of the containers was evaluated in the same manner as in Example 6. In this test, *S. aureaus* IFO 12732 was used as a test microorganism.

EXAMPLE 15

1)

Fifty parts of N,N-dimethylacrylamide, 31.7 parts of tris(trimethylsiloxy)silylpropyl methacrylate, 17 parts of 2,2,2-trifluoroethyl methacrylate, 1 part of ethylene glycol dimethacrylate, and 0.3 part of isopropyl percarbonate were mixed well, and the mixture was put in a glass test tube. The test tube was repeatedly purged with nitrogen for deaeration and heat-sealed in vacuo. The sealed test tube was heated at 30 for 10 hours; 40° C. for 5 hours; 50° C. for 5 hours; 60° C. for 3 hours; and 70° C. for 3 hours in warm water and then at 100° C. for 2 hours in an atmospheric furnace to conduct polymerization. The resulting resin rod was cut and polished to obtain several contact lenses.

2) Conversion:

To the resulting contact lenses were added 50.51 g (0.1300 mol) of trioctylphosphine to convert the functional group of the polymer to a phosphonium ion so that the compound shown in Table 34 (a compound of formula (2)) might exist on the surface of the lenses.

In the same manner as described above, except for replacing trioctylphosphine with various trialkylphosphines, the compound shown in Tables 35 to 37 (a compound of formula (1), (3) or (8), respectively) was added to the surface of a lens.

3) Swelling and Elution:

The resulting lenses were swollen with pure water, washed, and soaked in physiological saline to absorb a prescribed amount of water and also to complete elution of any soluble matter.

4) Measurement of Antimicrobial Activity:

The antimicrobial activity of the lens was evaluated in the same manner as in Example 6.

The results of measurement of antimicrobial activity obtained in Examples 6 to 15 are shown in the Tables below. "Control" in Examples 6 to 11 are a contact lenses having the same composition as the corresponding Example except that they contained no antimicrobial substance. "Control" in Examples 12 to 13 and 15 are a contact lenses which were not subjected to a surface treatment. "Control" in Example 14 are contact lens containers having the same composition as that of Example 14, except that they contained no antimicrobial substance.

TABLE 10

Antimicrobial Activity of Contact Lens

| Test Bacterium | Example No. | Number of Residual Cells/ml | | | |
|---|---|---|---|---|---|
| | | Initial | 0.5 hr | 1.0 hr | 2.0 hrs |
| E. coli | Example 6 | $7.1 \times 10^5$ | $3.6 \times 10^4$ | $1.1 \times 10^4$ | $1.1 \times 10^3$ |
| IFO 3806 | Control | $7.1 \times 10^5$ | $6.3 \times 10^5$ | $5.6 \times 10^5$ | $3.5 \times 10^5$ |
| S. aureaus | Example 6 | $2.5 \times 10^6$ | $1.6 \times 10^3$ | $4.0 \times 10^2$ | $1.2 \times 10^2$ |
| IFO 12732 | Control | $2.5 \times 10^6$ | $1.3 \times 10^6$ | $1.3 \times 10^5$ | $1.1 \times 10^5$ |

TABLE 11

Antimicrobial Activity of Contact Lens

| Test Bacterium | Example No. | Number of Residual Cells/ml | | | |
|---|---|---|---|---|---|
| | | Initial | 0.5 hr | 1.0 hr | 2.0 hrs |
| E. coli | Example 7 | $2.1 \times 10^5$ | $6.2 \times 10^3$ | $7.9 \times 10^2$ | $1.7 \times 10^2$ |
| IFO 3806 | Control | $2.1 \times 10^5$ | $2.4 \times 10^5$ | $2.5 \times 10^5$ | $1.3 \times 10^5$ |
| S. aureaus | Example 7 | $1.3 \times 10^6$ | $4.0 \times 10^3$ | $3.2 \times 10^2$ | 40 |
| IFO 12732 | Control | $1.3 \times 10^6$ | $1.0 \times 10^6$ | $7.5 \times 10^5$ | $6.3 \times 10^5$ |

TABLE 12

Antimicrobial Activity of Contact Lens
[Compound (3); $R^1 = R^2 = R^3 = C_8H_{17}$; $X = Cl; Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 8 | $1.7 \times 10^5$ | $5.1 \times 10^3$ | $1.4 \times 10^3$ | $6.3 \times 10^2$ |
| IFO 3806 | Control | $1.7 \times 10^5$ | $1.4 \times 10^5$ | $1.5 \times 10^5$ | $1.1 \times 10^5$ |
| S. aureaus | Example 8 | $5.1 \times 10^6$ | $4.0 \times 10^3$ | $3.2 \times 10^2$ | 40 |
| IFO 12732 | Control | $5.1 \times 10^6$ | $4.4 \times 10^6$ | $3.3 \times 10^6$ | $3.5 \times 10^5$ |

TABLE 13

Antimicrobial Activity of Contact Lens
[Compound (3); $R^1 = R^2 = R^3 = C_4H_9$; $X = Cl; Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 8 | $1.8 \times 10^5$ | $1.2 \times 10^3$ | $4.0 \times 10^5$ | $1.7 \times 10^5$ |
| IFO 3806 | Control | $1.8 \times 10^5$ | $1.4 \times 10^5$ | $7.0 \times 10^4$ | $5.7 \times 10^4$ |
| S. aureaus | Example 8 | $1.6 \times 10^6$ | $1.1 \times 10^6$ | $3.6 \times 10^5$ | $8.0 \times 10^4$ |
| IFO 12732 | Control | $1.6 \times 10^6$ | $2.0 \times 10^6$ | $2.1 \times 10^6$ | $6.4 \times 10^5$ |

TABLE 14

Antimicrobial Activity of Contact Lens
[Compound (3); $R^1 = R^2 = CH_3$; $R^3 = C_{16}H_{33}$; $X = Cl; Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 8 | $1.8 \times 10^5$ | $1.2 \times 10^3$ | $4.0 \times 10^5$ | $1.7 \times 10^5$ |
| IFO 3806 | Control | $1.8 \times 10^5$ | $1.4 \times 10^5$ | $7.0 \times 10^4$ | $5.7 \times 10^4$ |
| S. aureaus | Example 8 | $1.6 \times 10^6$ | $1.1 \times 10^6$ | $3.6 \times 10^5$ | $8.0 \times 10^4$ |
| IFO 12732 | Control | $1.6 \times 10^6$ | $2.0 \times 10^6$ | $2.1 \times 10^6$ | $6.4 \times 10^5$ |

TABLE 15

Antimicrobial Activity of Contact Lens
[Compound (1); $R^1 = R^2 = R^3 = C_8H_{17}$; $X = Cl; Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 9 | $7.1 \times 10^5$ | $9.8 \times 10^4$ | $2.4 \times 10^4$ | $9.3 \times 10^3$ |
| IFO 3806 | Control | $7.1 \times 10^5$ | $7.7 \times 10^5$ | $8.1 \times 10^5$ | $5.9 \times 10^5$ |
| S. aureaus | Example 9 | $2.2 \times 10^6$ | $2.6 \times 10^3$ | $1.5 \times 10^2$ | 0 |
| IFO 12732 | Control | $2.2 \times 10^6$ | $2.1 \times 10^6$ | $1.9 \times 10^6$ | $2.0 \times 10^5$ |

TABLE 16

Antimicrobial Activity of Contact Lens
[Compound (1); $R^1 = R^2 = R^3 = C_4H_9$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 9 | $7.1 \times 10^5$ | $8.2 \times 10^5$ | $4.7 \times 10^5$ | $2.5 \times 10^5$ |
| IFO 3806 | Control | $7.1 \times 10^5$ | $7.7 \times 10^5$ | $8.1 \times 10^5$ | $5.9 \times 10^5$ |
| S. aureaus | Example 9 | $2.2 \times 10^6$ | $3.0 \times 10^5$ | $1.1 \times 10^5$ | $6.2 \times 10^4$ |
| IFO 12732 | Control | $2.2 \times 10^6$ | $2.1 \times 10^6$ | $1.9 \times 10^6$ | $2.0 \times 10^6$ |

TABLE 17

Antimicrobial Activity of Contact Lens
[Compound (1); $R^1 = R^2 = CH_3$; $R^3 = C_{16}H_{33}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 9 | $7.1 \times 10^5$ | $5.6 \times 10^4$ | $1.4 \times 10^2$ | 0 |
| IFO 3806 | Control | $7.1 \times 10^5$ | $7.7 \times 10^5$ | $8.1 \times 10^5$ | $5.9 \times 10^5$ |
| S. aureaus | Example 9 | $2.2 \times 10^6$ | $2.0 \times 10^2$ | 0 | 0 |
| IFO 12732 | Control | $2.2 \times 10^6$ | $2.1 \times 10^6$ | $1.9 \times 10^6$ | $2.0 \times 10^6$ |

TABLE 18

Antimicrobial Activity of Contact Lens
[Compound (8); $R^1 = R^2 = R^3 = C_8H_{17}$; $X = Cl$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 10 | $7.1 \times 10^5$ | $1.4 \times 10^5$ | $3.6 \times 10^4$ | $2.8 \times 10^3$ |
| IFO 3806 | Control | $7.1 \times 10^5$ | $7.7 \times 10^5$ | $8.1 \times 10^5$ | $5.9 \times 10^5$ |
| S. aureaus | Example 10 | $2.2 \times 10^6$ | $5.0 \times 10^4$ | $2.3 \times 10^3$ | 4 |
| IFO 12732 | Control | $2.2 \times 10^6$ | $2.1 \times 10^6$ | $1.9 \times 10^6$ | $2.0 \times 10^6$ |

TABLE 19

Antimicrobial Activity of Contact Lens
[Compound (2); $R^1 = R^2 = R^3 = C_8H_{17}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 11 | $7.6 \times 10^5$ | $5.1 \times 10^3$ | 53 | 0 |
| IFO 3806 | Control | $7.6 \times 10^5$ | $3.6 \times 10^5$ | $2.2 \times 10^5$ | $1.1 \times 10^5$ |
| S. aureaus | Example 11 | $4.8 \times 10^6$ | 0 | 0 | 0 |
| IFO 12732 | Control | $4.8 \times 10^6$ | $1.0 \times 10^6$ | $7.9 \times 10^5$ | $6.5 \times 10^5$ |

TABLE 20

Antimicrobial Activity of Contact Lens
[Compound (2); $R^1 = R^2 = R^3 = C_4H_9$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 11 | $6.8 \times 10^4$ | $6.0 \times 10^4$ | $3.8 \times 10^4$ | $1.9 \times 10^4$ |
| IFO 3806 | Control | $6.8 \times 10^4$ | $6.2 \times 10^4$ | $6.9 \times 10^4$ | $6.9 \times 10^4$ |
| S. aureaus | Example 11 | $1.5 \times 10^4$ | $9.8 \times 10^3$ | $4.5 \times 10^3$ | $1.1 \times 10^3$ |
| IFO 12732 | Control | $1.5 \times 10^4$ | $1.6 \times 10^4$ | $1.7 \times 10^4$ | $6.9 \times 10^3$ |

TABLE 21

Antimicrobial Activity of Contact Lens
[Compound (2); $R^1 = R^2 = CH_3$; $R^3 = C_{16}H_{33}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 11 | $6.8 \times 10^4$ | $5.2 \times 10^2$ | $1.3 \times 10$ | $1.9 \times 10^4$ |
| IFO 3806 | Control | $6.8 \times 10^4$ | $6.2 \times 10^4$ | $6.9 \times 10^4$ | $6.9 \times 10^4$ |
| S. aureaus | Example 11 | $1.5 \times 10^4$ | 0 | 0 | 0 |
| IFO 12732 | Control | $1.5 \times 10^4$ | $1.6 \times 10^4$ | $1.7 \times 10^4$ | $6.9 \times 10^3$ |

TABLE 22

Antimicrobial Activity of Contact Lens
[Compound (2); $R^1 = R^2 = R^3 = C_8H_{17}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 12 | $2.1 \times 10^6$ | 17 | 0 | 0 |
| IFO 3806 | Control | $2.1 \times 10^6$ | $2.0 \times 10^5$ | $1.8 \times 10^5$ | $1.9 \times 10^5$ |
| S. aureaus | Example 12 | $5.4 \times 10^5$ | 0 | 0 | 0 |
| IFO 12732 | Control | $5.4 \times 10^5$ | $3.0 \times 10^5$ | $1.7 \times 10^5$ | $2.2 \times 10^5$ |

TABLE 23

Antimicrobial Activity of Contact Lens
[Compound (1); $R^1 = R^2 = R^3 = C_8H_{17}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli | Example 12 | $6.8 \times 10^4$ | $4.6 \times 10^3$ | 0 | 0 |
| IFO 3806 | Control | $6.8 \times 10^4$ | $6.2 \times 10^4$ | $6.9 \times 10^4$ | $6.9 \times 10^4$ |
| S. aureaus | Example 12 | $1.5 \times 10^4$ | $1.6 \times 10^2$ | 0 | 0 |
| IFO 12732 | Control | $1.5 \times 10^4$ | $1.6 \times 10^4$ | $1.7 \times 10^4$ | $6.9 \times 10^3$ |

TABLE 24

Antimicrobial Activity of Contact Lens
[Compound (3); $R^1 = R^2 = R^3 = C_8H_{17}$; $X = Cl$; $Y = CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 12 | $6.8 \times 10^4$ | $4.7 \times 10^3$ | 69 | 0 |
| | Control | $6.8 \times 10^4$ | $6.2 \times 10^4$ | $6.9 \times 10^4$ | $6.9 \times 10^4$ |
| S. aureus IFO 12732 | Example 12 | $1.5 \times 10^4$ | $1.6 \times 10^2$ | 0 | 0 |
| | Control | $1.5 \times 10^4$ | $1.6 \times 10^4$ | $1.7 \times 10^4$ | $6.9 \times 10^3$ |

TABLE 25

Antimicrobial Activity of Contact Lens
[Compound (8); $R^1=R^2=R^3=C_8H_{17}$; $X=Cl$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 12 | $6.8 \times 10^4$ | $5.3 \times 10^3$ | $3.0 \times 10^2$ | 0 |
| | Control | $6.8 \times 10^4$ | $6.2 \times 10^4$ | $6.9 \times 10^4$ | $6.9 \times 10^4$ |
| S. aureus IFO 12732 | Example 12 | $1.5 \times 10^4$ | $1.2 \times 10^3$ | 37 | 0 |
| | Control | $1.5 \times 10^4$ | $1.6 \times 10^4$ | $1.7 \times 10^4$ | $6.9 \times 10^3$ |

TABLE 26

Antimicrobial Activity of Contact Lens
[Compound (8); $R^1=R^2=R^3=C_8H_{17}$; $X=Cl$]
$R^1=R^2=R^3=C_8H_{17}$; $X=Cl$; $Y=CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 13 | $2.1 \times 10^6$ | 0 | 0 | 0 |
| | Control | $2.1 \times 10^6$ | $2.0 \times 10^5$ | $1.8 \times 10^5$ | $1.9 \times 10^5$ |
| S. aureus IFO 12732 | Example 13 | $5.4 \times 10^5$ | 0 | 0 | 0 |
| | Control | $5.4 \times 10^5$ | $30 \times 10^5$ | $1.7 \times 10^5$ | $2.2 \times 10^5$ |

TABLE 27

Antimicrobial Activity of Contact Lens
[Compound (1); $R^1=R^2=R^3=C_8H_{17}$; $X=Cl$; $Y=CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 13 | $6.5 \times 10^5$ | 0 | 0 | 0 |
| | Control | $6.5 \times 10^5$ | $8.1 \times 10^5$ | $7.9 \times 10^5$ | $3.5 \times 10^5$ |
| S. aureus IFO 12732 | Example 13 | $1.2 \times 10^6$ | 0 | 0 | 0 |
| | Control | $1.2 \times 10^6$ | $9.4 \times 10^5$ | $6.6 \times 10^5$ | $1.1 \times 10^6$ |

TABLE 28

Antimicrobial Activity of Contact Lens
[Compound (3); $R^1=R^2=R^3=C_8H_{17}$; $X=Cl$; $Y=CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 13 | $6.5 \times 10^5$ | 58 | 0 | 0 |
| | Control | $6.5 \times 10^5$ | $8.1 \times 10^5$ | $7.9 \times 10^5$ | $3.5 \times 10^5$ |
| S. aureus IFO 12732 | Example 13 | $1.2 \times 10^6$ | $2.5 \times 10^2$ | 0 | 0 |
| | Control | $1.2 \times 10^6$ | $9.4 \times 10^5$ | $6.6 \times 10^5$ | $1.1 \times 10^6$ |

TABLE 29

Antimicrobial Activity of Contact Lens
[Compound (8); $R^1=R^2=R^3=C_8H_{17}$; $X=Cl$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 13 | $6.5 \times 10^5$ | $6.1 \times 10^4$ | 0 | 0 |
| | Control | $6.5 \times 10^5$ | $8.1 \times 10^5$ | $7.9 \times 10^5$ | $3.5 \times 10^5$ |
| S. aureus IFO 12732 | Example 13 | $1.2 \times 10^6$ | $4.8 \times 10^3$ | 0 | 0 |
| | Control | $1.2 \times 10^6$ | $9.4 \times 10^5$ | $6.6 \times 10^5$ | $1.1 \times 10^6$ |

TABLE 30

Antimicrobial Activity of Contact Lens Container
[Compound (8); $R^1=R^2=R^3=C_8H_{17}$; $X=Cl$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 14 | $4.4 \times 10^6$ | $5.2 \times 10^5$ | $1.0 \times 10^4$ | $3.1 \times 10^3$ |
| | Control | $4.4 \times 10^6$ | $4.2 \times 10^6$ | $4.5 \times 10^5$ | $1.1 \times 10^5$ |
| S. aureus IFO 12732 | Example 14 | $9.5 \times 10^6$ | $4.3 \times 10^5$ | 5 | 0 |
| | Control | $9.5 \times 10^6$ | $9.0 \times 10^6$ | $3.4 \times 10^5$ | $2.1 \times 10^4$ |

TABLE 31

Antimicrobial Activity of Contact Lens Container
[Compound (1); $R^1=R^2=R^3=C_8H_{17}$; $X=Cl$; $Y=CH_2$]

| Test Bacterium | Example No. | Number of Residual Cells/ml | | | |
|---|---|---|---|---|---|
| | | Initial | 0.5 hr | 1.0 hr | 2.0 hrs |
| E. coli IFO 3806 | Example 14 | $9.5 \times 10^3$ | $2.4 \times 10^3$ | $1.0 \times 10^3$ | 17 |
| | Control | $9.5 \times 10^3$ | $6.3 \times 10^3$ | $7.9 \times 10^3$ | $1.2 \times 10^2$ |
| S. aureus IFO 12732 | Example 14 | $3.1 \times 10^4$ | $2.0 \times 10^4$ | $6.6 \times 10^2$ | 0 |
| | Control | $3.1 \times 10^4$ | $9.8 \times 10^3$ | $30 \times 10^3$ | $6.2 \times 10^2$ |

TABLE 32

Antimicrobial Activity of Contact Lens Container

Test [Compound (3); $R^1=R^2=R^3=C_8H_{17}$; X=Cl; Y=CH$_2$]

| Bacterium | Example No. | Initial | 0.5 hr | 1.0 hr | 2.0 hrs |
|---|---|---|---|---|---|
| E. coli IFO 3806 | Example 14 | $9.5 \times 10^3$ | $4.3 \times 10^3$ | $5.0 \times 10^3$ | 25 |
|  | Control | $9.5 \times 10^3$ | $6.3 \times 10^3$ | $7.9 \times 10^3$ | $1.2 \times 10^2$ |
| S. aureaus IFO 12732 | Example 14 | $3.1 \times 10^4$ | $2.1 \times 10^4$ | $3.2 \times 10^2$ | 0 |
|  | Control | $3.1 \times 10^4$ | $9.8 \times 10^3$ | $3.0 \times 10^3$ | $1.3 \times 10^3$ |

TABLE 33

Antimicrobial Activity of Contact Lens Container

Test [Compound (7); $R^1=R^2=R^3=C_8H_{17}$; X=Cl]

| Bacterium | Example No. | Initial | 0.5 hr | 1.0 hr | 2.0 hrs |
|---|---|---|---|---|---|
| E. coli IFO 3806 | Example 14 | $9.5 \times 10^3$ | $6.3 \times 10^3$ | $1.5 \times 10^3$ | 79 |
|  | Control | $9.5 \times 10^3$ | $6.3 \times 10^3$ | $7.9 \times 10^3$ | $1.2 \times 10^2$ |
| S. aureaus IFO 12732 | Example 14 | $3.1 \times 10^4$ | $1.8 \times 10^4$ | $7.2 \times 10^2$ | 0 |
|  | Control | $3.1 \times 10^4$ | $9.8 \times 10^3$ | $3.0 \times 10^3$ | $1.3 \times 10^3$ |

TABLE 34

Antimicrobial Activity of Contact Lens

Test [Compound (8); $R^1=R^2=R^3=C_8H_{17}$; X=Cl]

| Bacterium | Example No. | Initial | 0.5 hr | 1.0 hr | 2.0 hrs |
|---|---|---|---|---|---|
| E. coli IFO 3806 | Example 15 | $2.1 \times 10^6$ | 0 | 0 | 0 |
|  | Control | $2.1 \times 10^6$ | $2.0 \times 10^5$ | $1.8 \times 10^5$ | $1.9 \times 10^5$ |
| S. aureaus IFO 12732 | Example 15 | $5.4 \times 10^5$ | 0 | 0 | 0 |
|  | Control | $5.4 \times 10^5$ | $3.0 \times 10^5$ | $1.7 \times 10^5$ | $2.2 \times 10^5$ |

TABLE 35

Antimicrobial Activity of Contact Lens

Test [Compound (1); $R^1=R^2=R^3=C_8H_{17}$; X=Cl; Y=CH$_2$]

| Bacterium | Example No. | Initial | 0.5 hr | 1.0 hr | 2.0 hrs |
|---|---|---|---|---|---|
| E. coli IFO 3806 | Example 15 | $4.1 \times 10^4$ | 0 | 0 | 0 |
|  | Control | $4.1 \times 10^4$ | $1.5 \times 10^5$ | $4.2 \times 10^4$ | $3.0 \times 10^4$ |
| S. aureaus IFO 12732 | Example 15 | $2.7 \times 10^5$ | 0 | 0 | 0 |
|  | Control | $2.7 \times 10^5$ | $1.9 \times 10^5$ | $1.1 \times 10^5$ | $1.8 \times 10^5$ |

TABLE 36

Antimicrobial Activity of Contact Lens

Test [Compound (3); $R^1=R^2=R^3=C_8H_{17}$; X=Cl; Y=CH$_2$]

| Bacterium | Example No. | Initial | 0.5 hr | 1.0 hr | 2.0 hrs |
|---|---|---|---|---|---|
| E. coli IFO 3806 | Example 15 | $4.1 \times 10^4$ | 25 | 0 | 0 |
|  | Control | $4.1 \times 10^4$ | $1.5 \times 10^5$ | $4.2 \times 10^4$ | $3.0 \times 10^4$ |
| S. aureaus IFO 12732 | Example 15 | $2.7 \times 10^5$ | $2.0 \times 10^2$ | 0 | 0 |
|  | Control | $2.7 \times 10^5$ | $1.9 \times 10^5$ | $1.1 \times 10^5$ | $1.8 \times 10^5$ |

TABLE 37

Antimicrobial Activity of Contact Lens

[Compound (8); $R^1=R^2=R^3=C_8H_{17}$; X=Cl]

Test Number of Residual Cells/ml

| Bacterium | Example No. | Initial | 0.5 hr | 1.0 hr | 2.0 hrs |
|---|---|---|---|---|---|
| E. coli IFO 3806 | Example 15 | $4.1 \times 10^4$ | $4.0 \times 10^2$ | 0 | 0 |
|  | Control | $4.1 \times 10^4$ | $1.5 \times 10^4$ | $4.2 \times 10^4$ | $3.0 \times 10^4$ |
| S. aureaus IFO 12732 | Example 15 | $2.7 \times 10^5$ | $5.0 \times 10^3$ | $7.9 \times 10^2$ | 0 |
|  | Control | $2.7 \times 10^5$ | $1.9 \times 10^5$ | $1.1 \times 10^5$ | $1.8 \times 10^5$ |

When each of the contact lenses and contact lens containers prepared in the foregoing Examples were boiled, no elution of the antimicrobial substance therefrom was observed.

INDUSTRIAL APPLICABILITY

According to the present invention, an antimicrobial polymer having a broad antimicrobial spectrum and with sufficient antimicrobial effect after a short cotact time can be obtained. The polymer of the present invention has high antimicrobial activity and is useful as an antimicrobial polymer. The antimicrobial polymer of the present invention is useful as antimicrobial agents for external use, antimicrobial agents for hygienic finishing of fiber, fabric, etc., coatings, constructive materials, antimicrobial agents for swimming pool or industrial water, antimicrobial resin household articles, contact lenses, plastic articles for contact lens care, and the like. The antimicrobial polymer may be rendered antistatic, and flame or stain resistant. The antimicrobial polymer of the invention may be shaped into spheres or pellets and packed into a column, etc. for use as a filter for sterilization of air or water.

The contact lens and contact lens-care articles according to the present invention barely suffer from contamination with microorganisms such as bacteria and fungi and therefore need no tedious handling for sterilization. In addition, the contact lens of the present invention possesses other required properties, i.e., optical properties, processability, strength, and safety.

We claim:

1. A contact lens mainly comprising an antimicrobial resin obtained by copolymerizing a polymerizable monomer and a phosphonium salt vinyl monomer.

2. A contact lens endowed with antimicrobial activity which is obtained by graft polymerizing a phosphonium salt vinyl monomer to a contact lens resin.

3. A contact lens-care article mainly comprising an antimicrobial resin obtained by copolymerizing a polymerizable monomer and a phosphonium salt vinyl monomer.

4. A contact lens-care article as claimed in claim 3, wherein said contact lens-care article is a container for contact lenses, a container for a soaking solution for contact lenses, a container for a contact lens cleaner, a container for a cleaning soaking solution for contact lenses, a container for water for dissolving, a mat for preventing contact lenses from being misplaced during washing, a contact lens case, or a contact lens compact case.

5. A contact lens as claimed in claim 1 or 2, wherein said phosphonium salt vinyl monomer is at least one compound selected from the group consisting of a compound represented by formula (8):

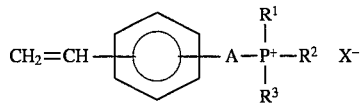

a compound represented by formula (1):

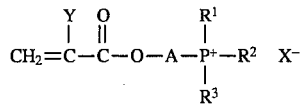

a compound represented by formula (2):

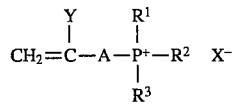

and a compound represented by formula (3):

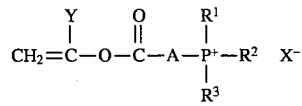

wherein A represents a linear or branched alkylene group; Y represents a hydrogen atom, a lower alkyl group or an aryl group; $R^1$, $R^2$, and $R^3$, which may be the same or different, each represents a hydrogen atom, a linear or branched alkyl group having from 1 to 18 carbon atoms, an aryl group, an aralkyl group, or an alkyl, aryl or aralkyl group which is substituted with a hydroxyl group or an alkoxy group; and $X^-$ represents an anion.

6. A contact lens-care article as claimed in claim 3 or 4, wherein said phosphonium salt vinyl monomer is at least one compound of claim 5.

7. A method for providing antimicrobial property to an object in need thereof, comprising contacting said object with an effective amount of a bactericidal composition comprising a polymer obtained by homo- or copolymerizing at least one phosphonium salt vinyl monomer selected from the group consisting of a compound represented by formula (1):

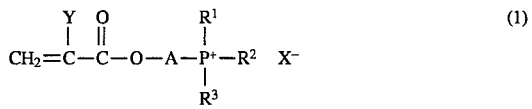

a compound represented by formula (2):

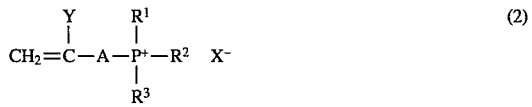

and a compound represented by formula (3):

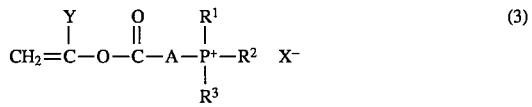

wherein A represents a linear or branched alkylene group; Y represents a hydrogen atom, a lower alkyl group or an aryl group; $R^1$, $R^2$, and $R^3$, which may be the same or different, each represents a hydrogen atom, a linear or branched alkyl group having from 1 to 18 carbon atoms, an aryl group, an aralkyl group, or an alkyl, aryl or aralkyl group which is substituted with a hydroxyl group or an alkoxy group; and $X^-$ represents an anion, either among themselves or with other copolymerizable monomers.

8. A method for providing antimicrobial property to an object in need thereof, comprising contacting said object with an effective amount of bactericidal composition comprising a polymer obtained by homo- or copolymerizing at least one phosphonium salt vinyl monomer selected from the group consisting of a compound represented by formula (4):

a compound represented by formula (5):

and a compound represented by formula (6):

wherein A represents a linear or branched alkylene group; Y represents a hydrogen atom, a lower alkyl group or an aryl group; and X represents a monovalent atom or residual group capable of becoming an anion, either among themselves of with other copolymerizable monomers and converging the functional group of the resulting polymer to a phosphonium ion with a triorganophosphite represented by formula (7):

wherein $R^1$, $R^2$, and $R^3$, which may be the same or different, each represents a hydrogen atom, a linear or branched alkyl group having 1 to 18 carbon atoms, an aryl group, an aralkyl group, or an alkyl, aryl or aralkyl group which is substituted with a hydroxyl group or an alkoxy group.

* * * * *

UNITED STATES PATENT AND TRADEMARK OFFICE
CERTIFICATE OF CORRECTION

PATENT NO. : 5,520,910
DATED : May 28, 1996
INVENTOR(S) : Kazukichi HASHIMOTO, et al.

It is certified that error appears in the above-indentified patent and that said Letters Patent is hereby corrected as shown below:

On the title page, Item [87], the PCT publication date should read:

-- [87] PCT Pub. No: WO95/02617
       PCT Pub. Date: Jan 26, 1995 --

Signed and Sealed this

Twenty-fourth Day of September, 1996

*Attest:*

BRUCE LEHMAN

*Attesting Officer*  *Commissioner of Patents and Trademarks*